United States Patent
Bolz et al.

[11] Patent Number: 5,871,511
[45] Date of Patent: Feb. 16, 1999

[54] IMPLANTABLE APPARATUS FOR THE EARLY DIAGNOSIS AND SUPPRESSION OF TACHYCARDIA IN THE HEART

[75] Inventors: Armin Bolz, Erlangen; Klaus Bartels, Berlin; Erhard Flach, Berlin; Rainer Hintsche, Berlin; Manfred Paeschke, Basdorf, all of Germany

[73] Assignee: Biotronik Mess- und Therapiegeräte GmbH & Co., Berlin, Germany

[21] Appl. No.: 929,085

[22] Filed: Sep. 15, 1997

[30] Foreign Application Priority Data

Sep. 20, 1996 [DE] Germany .................. 196 38 581.4

[51] Int. Cl.$^6$ .................................................. A61N 1/365
[52] U.S. Cl. .................................................. 607/14
[58] Field of Search .................. 607/14; 600/510

[56] References Cited

U.S. PATENT DOCUMENTS 4,969,468  11/1990  Byers et al. .
5,476,503  12/1995  Yang .

FOREIGN PATENT DOCUMENTS 34 15 732  10/1984  Germany .

OTHER PUBLICATIONS

Spicer, M. et al., "Cardiac stimulator for the study of refractory period control using current pulses of programmable duration and shape.", Medical & Biological Engineering & Computing, pp. 377–383 (Jul. 1992).

Jones, Janice L. et al., "The mechanism of defibrillation and cardioversion.", Proceedings of the IEEE, vol. 84, No. 3, pp. 392–403 (Mar. 1996).

Liang, David H. et al., "A method for evaluating the selectivity of electrodes implanted for nerve stimulation.", IEEE Transactions on Biomedical Engineering, vol. 38, No. 5, pp. 443–449 (May 1991).

Holm, Magnus et al., "A new method for analysis of atrial activation during chronic atrial fibrillation in man.", IEEE Transactions on Biomedical Engineering, vol. 43, No. 2, pp. 198–210 (February 1996).

Paeschke, M. et al., "Properties of interdigital electrode arrays with different geometries.", Analytica Chimica Acta, vol. 205, pp. 126–136 (1995).

*Primary Examiner*—William E. Kamm
*Attorney, Agent, or Firm*—Browdy and Neimark

[57] ABSTRACT

An implantable apparatus for the early diagnosis of tachycardia in the heart is provided with a microelectrode array, which is in contact with the cardiac muscle tissue, for detecting stimulus conduction potentials in the cardiac muscle tissue, a measuring device, which is in connection with the microelectrode array, for determining the refractory time of the cardiac muscle cells in the monitored cardiac region, a measuring device, which is in connection with the microelectrode array, for determining the stimulus conduction velocity in the monitored cardiac muscle region, a computing device for determining the product value of the refractory time and the stimulus conduction velocity, a comparator for comparing the product value with a tachycardia threshold, any falling short of the tachycardia threshold signaling a condition of the heart in risk of tachycardia, a stimulation arrangement for generating antitachycardia stimulation upon detection of a condition of risk of tachycardia in particular via the microelectrode array, and a control unit for controlling the measuring and evaluation processes within the apparatus.

11 Claims, 2 Drawing Sheets

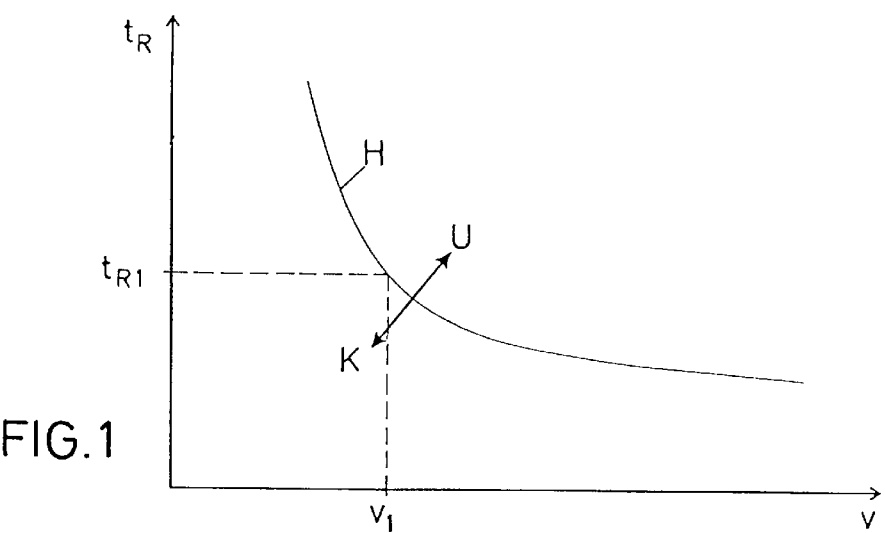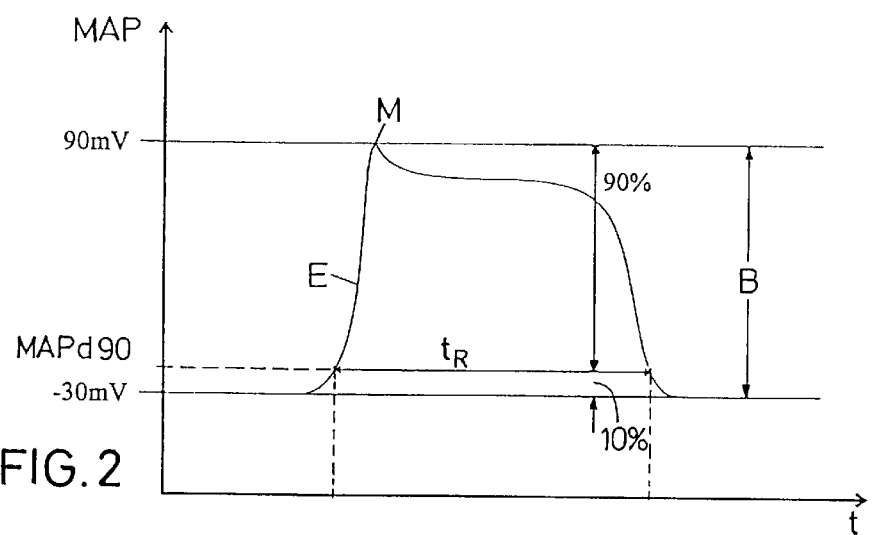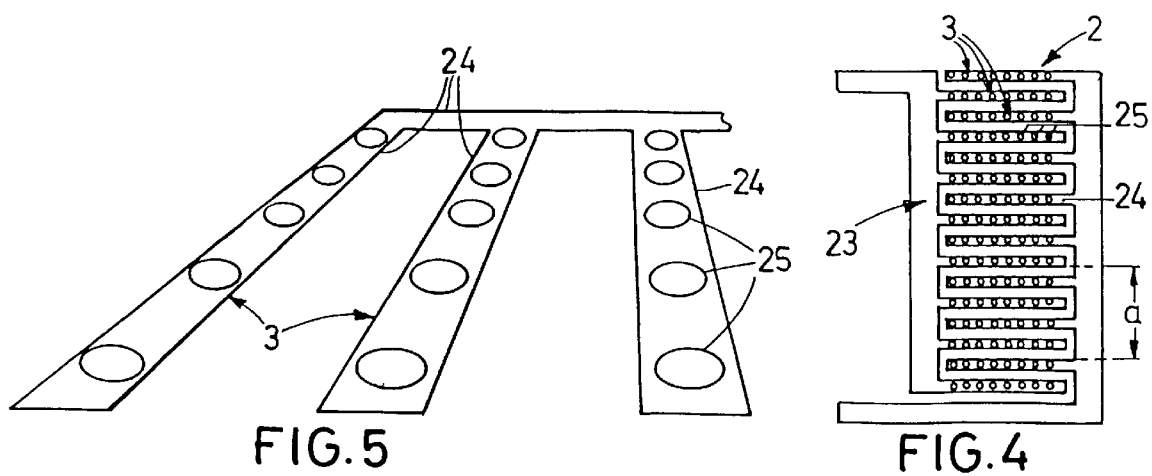

IMPLANTABLE APPARATUS FOR THE EARLY DIAGNOSIS AND SUPPRESSION OF TACHYCARDIA IN THE HEART

BACKGROUND OF THE INVENTION

1. Field of the Invention

The invention relates to an implantable apparatus for the early diagnosis and suppression of tachycardia in the heart.

2. Background Art

As for the background of the invention, a short explanation is necessary of the cardiac arrhythmias designated as tachycardia, in which the heart rate rises beyond a physiologically reasonable degree. In this case, the individual contractions of the heart take place so fast that no sufficient quantity of blood is transported per contraction. The heart rate increase is over-compensated by the decrease in volume of the heartbeat.

Fundamentally, ventricular tachycardia conditions are dangerous, since the pumping capacity of the heart is mainly performed by the ventriculus, while the atrium contributes to blood conveyance only to a very limited degree.

Conditions of ventricular tachycardia can be subdivided in varying degrees of severity. A first stage is characterized by changes in the morphology of the electric stimulus signals of the cardiac muscle cells and by irregularity in the slightly increased cardiac rhythm.

A second stage is the so-called ventricular flutter at a heart rate that has not yet risen to a critical degree. The decrease of the pumping capacity can however lead to a patient's syncope.

The most serious stage is the so-called ventricular fibrillation, in which case the drastic decrease of the pumping capacity leads to the death of a patient within a very short time.

To date, various measures have been taken for tachycardia therapy, adapted to the degree of severity of tachycardia. At a less critical stage, the setting in of tachycardia is frequently suppressed by so-called antitachycardia stimulation at amplitudes of some volts which is customary for heart pacemakers. The heart beating stably but too rapidly is "caught up", to which end stimulation pulses at certain time intervals are used. The prerequisite for the success of such a moderate therapy is the timely recognition and classification of such a condition of tachycardia.

In the case of ventricular fibrillation, the only thing that works is as a rule a defibrillation shock of some hundreds of volts, if this potential can be applied directly in the heart. Defibrillation shocks applied extracorporally—for example via chest electrodes—even need amplitudes of some kV.

If successful, a defibrillation shock leads to electric excitation of all cardiac muscle cells so that subsequently, all the cells find themselves in the so-called refractory phase. During this refractory phase, which is to be designated as a "dead period", any stimulus conduction within the heart is interrupted, even that one previously leading to fibrillation. The latter may base on circulating self-excitation, in which an excitation front circulates cyclically around a pathologically disfigured spot in the cardiac tissue—for instance an infarction scar.

Summing up, it may be said that the defibrillation shock is sort of a "reset" of the entire cardiac muscle apparatus which is very drastic and painful to the patient. Therefore, any effort should be made for conditions of tachycardia to be diagnosed as early as possible so that measures can be taken to prevent fibrillations from setting in.

However, the detection of high heart rates alone is not sufficient for this early diagnosis, since, in particular in the range of low heart rates, tachycardia conditions cannot be distinguished from natural increases of the heart rate as a result of physical stress. This is why the prior art mainly proceeds from two objectives for the early diagnosis of tachycardia. On the one hand, this consists in the evaluation, implemented on a heart pacemaker, of the so-called heart rate variability in ECG diagrams. Irregularities or certain acceleration patterns of the cardiac rhythm are to be recognized, which occur regularly at the beginning of the virtual tachycardia condition. Drawbacks of this method reside in the comparatively high requirements of computing and storing capacity, which today's implants cannot comply with sufficiently.

On the other hand, early tachycardia diagnosis makes use of an evaluation of the action potentials of cardiac muscle cells. Their morphology is subject to certain modifications already very early before the beginning of tachycardia. However, the implementation of such evaluation methods is not put into practice for lack of adequate findings, and presumably, the requirements on the computing and storing capacities of today's standards will again be too high for it to be possible to implement the corresponding method on an implant.

SUMMARY OF THE INVENTION

It is the object of the invention to embody an implantable apparatus by the aid of which the early diagnosis and suppression of tachycardia is reliably feasible.

To attain this object, provision is made for an implantable apparatus which is provided with

- a microelectrode array, which is in contact with the cardiac muscle tissue, for detecting stimulus conduction potentials in the cardiac muscle tissue,
- a measuring device, which is in connection with the microelectrode array, for determining the refractory time of the cardiac muscle cells in the monitored cardiac region,
- a measuring device, which is in connection with the microelectrode array, for determining the stimulus conduction velocity in the monitored region of the cardiac muscle,
- a computing device for determining the product value of the refractory time and the stimulus conduction velocity,
- a comparator for comparing the product value with a tachycardia threshold, any falling short of the tachycardia threshold signaling a condition of the heart in risk of tachycardia,
- a stimulation arrangement for generating antitachycardia stimulation upon detection of a condition of risk of tachycardia in particular via the microelectrode array, and
- a control unit for controlling the measuring and evaluation processes within the apparatus.

The invention proceeds from a different approach to early tachycardia diagnosis. Examinations have shown that the relation of the stimulus conduction velocity within the cardiac muscle tissue to the refractory time of the cardiac muscle cells is to be used as a critical variable for early tachycardia diagnosis. It has been found that cardiac conditions of risk of tachycardia are characterized by the fact that the product value of the stimulus conduction velocity and refractory time falls short of a certain threshold value, which is to be designated as the tachycardia threshold in the following. This can be explained diagrammatically, reference being made to the exemplary embodiment.

If, according to the invention, the refractory time and the stimulus conduction velocity in the monitored cardiac tissue are sensed by a microelectrode array, a comparison of the product value of these two variables determined by the computing device with the tachycardia threshold will be sufficient to decide whether the heart is in a condition of risk of tachycardia. This can be carried out automatically by the implanted apparatus, after which anti-tachycardia stimulations are generated if necessary by way of a stimulation arrangement. The classification, in terms of danger to the patient, of a condition in risk of tachycardia can also take place automatically on the basis of threshold values and an appropriate therapy can be selected, based on this.

Preferred designs, further features, details and advantages of the invention will become apparent from the sub-claims and the ensuing description of an exemplary embodiment of the subject matter of the invention, taken in conjunction with the drawing:

BRIEF DESCRIPTION OF THE DRAWING

FIG. 1 is a curve diagram illustrating the connection between the stimulus conduction velocity and the refractory time in the case of early tachycardia diagnosis according to the invention, FIG. 2 is a time-dependency diagram of the monophase action potential of cardiac muscle cells, FIG. 4 is a plan view of a microelectrode array of the apparatus according to FIG. 3, and FIG. 5 is a perspective illustration, on an enlarged scale, of individual electrode arms of the microelectrode array according to FIG. 4.

DESCRIPTION OF THE PREFERRED EMBODIMENT

Figure 3:
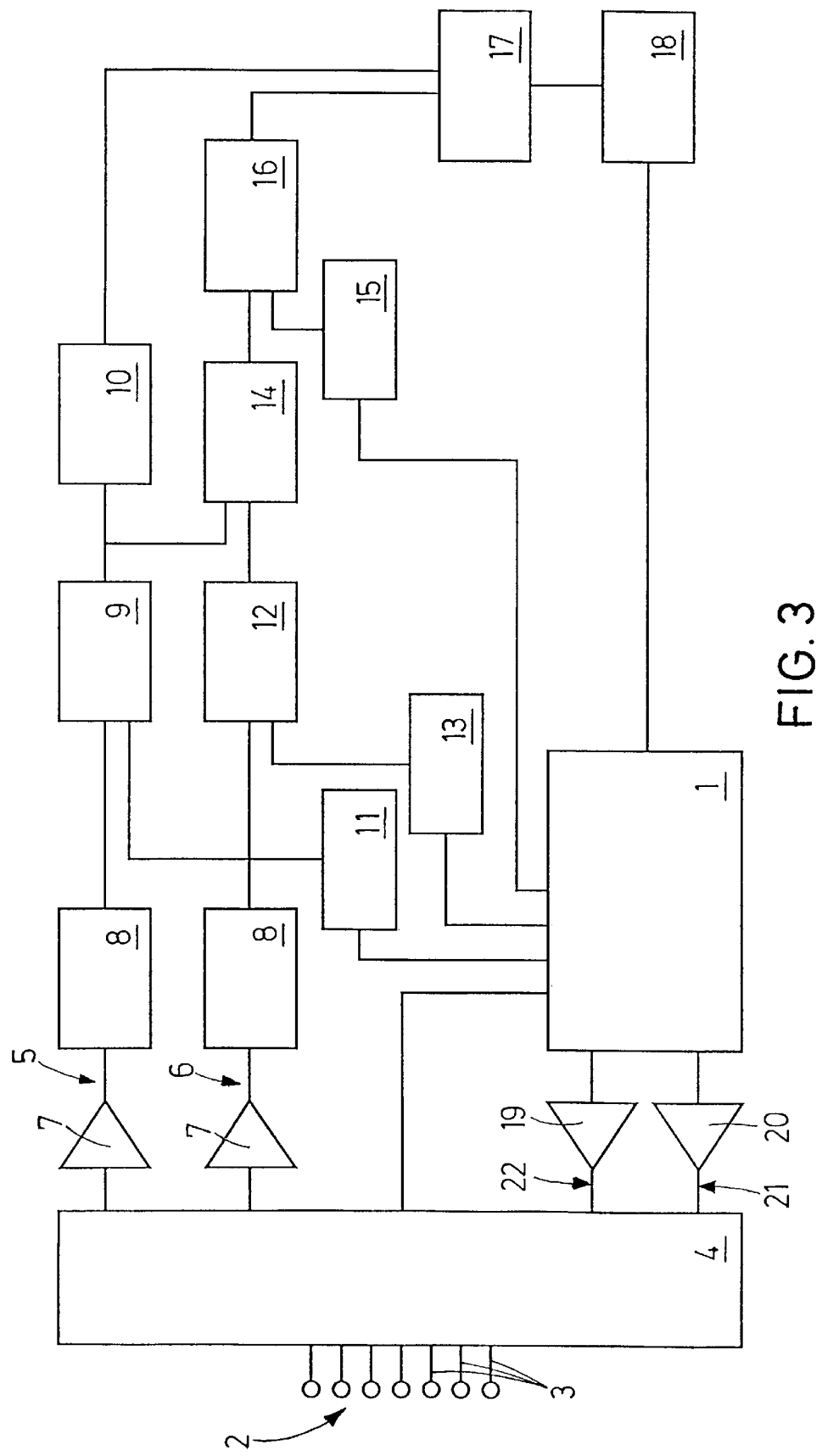
FIG. 3 is a block diagram of an apparatus according to the invention for the early diagnosis and suppression of tachycardia.

In the diagram according to FIG. 1, the stimulus conduction velocity v in the monitored cardiac muscle tissue is laid off as ordinate and the refractory time $t_R$ is qualitatively laid off as abscissa. The hyperbola H recorded in the diagram symbolizes the tachycardia threshold T, $$v \times t_R < T$$

applying to critical cardiac conditions. In the case of critical cardiac conditions, the product of the two variables v and $t_R$ is in the range K below the hyperbola H. For non-critical conditions, the product is in the range U above the hyperbola H. In practice this means that for a certain value $t_{R1}$ of the refractory time, the stimulus conduction velocity must be higher than a threshold $v_1$. In this case, stimulus conduction is so rapid that, in the case of an encircling, "circulating" excitation front E, the latter will reach the starting cell still during the refractory time. Thus, no self-excited stimulation can take place, which would lead to a tachycardia condition. If the stimulus conduction velocity v is lower than the critical value $v_1$, then the excitation front E is so slow that it will reach the said starting cell only after expiration of the refractory time, whereby the cell is again stimulated and a condition of tachycardia can set in.

Based on FIG. 2, the definition of the refractory time $t_R$ is to be explained. This diagram illustrates the so-called monophase action potential MAP of a cardiac muscle cell laid off as opposed to the time t. The MAP shows the excitation front E of the cell in the form of the steeply ascending flank. After the potential maximum M of typically 90 mV, the MAP decreases in the form of the curve illustrated to the equilibrium rest potential of typically −30 mV.

As seen in FIG. 2, the refractory time $t_R$ is defined as the period within which the value of the MAP exceeds 10% of the absolute MAP band width B (FIG. 2) (the so-called "MAPd90 value").

Measurement of the stimulus conduction velocity v and the refractory time $t_R$ takes place by means of a single microelectrode gate 23, which still remains to be explained in connection with FIGS. 4 and 5. By reference to FIG. 3, the structure of apparatus according to the invention for early tachycardia diagnosis is to be explained first.

According to the functional diagram of FIG. 3, the core of the apparatus is a control unit 1, which is put into practice in usual manner on a microprocessor base and which controls the measuring and evaluation processes within the apparatus by corresponding operational programs, which will still be explained in detail.

For the detection of the stimulus conduction potentials in the cardiac muscle tissue, provision is made for a microelectrode array 2, which is in contact with the cardiac muscle tissue and comprises electrode arms 3 illustrated in FIGS. 4 and 5 and only diagrammatically outlined in FIG. 3. The microelectrode array 2 can be positioned (not shown) on an electrode probe to be inserted into the ventriculus or atrium of the right side of the heart, as is known for electrode probes of heart pacemakers or defibrillators.

A connecting unit 4, which is controlled by the control unit 1, serves for selecting a pair of electrode arms 3 activated for measurement. In this way, two certain electrode arms 3 of the microelectrode array 2 can be connected to the two input channels 5, 6 of the apparatus. In both input channels 5, 6, input amplifiers 7 and band-pass filters 8 are interconnected for signal processing. A first threshold comparator 9 is allocated to the input channel 5 and a refractory time function element 10 is again allocated to the comparator 9. The input channel 5 and the threshold comparator 9 and the refractory time function element 10 virtually form a measuring device for determination of the refractory time of cardiac muscle cells. To this end, the control unit 1 gives the threshold MAPd90 via a threshold preset device 11 to the threshold comparator 9 and this threshold MAPd90 is compared with the MAP determined by the microelectrode array 2. The refractory time function element 10 determines the period within which the MAP value exceeds the MAPd90 value, which is seen in FIG. 2. By definition, the duration of this period corresponds to the refractory time $t_R$.

Allocated to the second input channel 6 is a second threshold comparator 12, to which again the MAPd90 value is given via the threshold preset device 13 as a threshold for the computation of the stimulus conduction time. The two threshold comparators 9 and 12 are connected with another time function element, namely the stimulus conduction time function element 14, which determines the period of time which passes between the point of time when the MAPd90 threshold is reached in the first and second threshold comparator 9 and 12. This period of time corresponds to the period needed by the excitation front E from one selected electrode arm 3 to the second selected electrode arm 3. By way of the control unit 1, the distance a (FIG. 4) between these two electrode arms 3 can be fetched from a storage (not shown) so that by means of this preset distance 15 and the stimulus conduction time determined by the stimulus conduction time function element 14, the stimulus conduction velocity can be computed as a quotient of these variables in a computing element 16. The second input channel 6 comprising the threshold comparator 9, the stimulus conduction time function element 14, the preset distance 15 and the computing element 16 virtually serves as a measuring device for the determination of the stimulus conduction velocity in the monitored cardiac muscle region.

The values determined by the refractory time function element 10 and the computing element 16 for the stimulus conduction velocity v in the monitored cardiac muscle region and the refractory time of the cardiac muscle cells there situated are supplied to a computing device 17 which determines the product of these. The third threshold comparator 18 compares whether this product is higher or lower than a tachycardia threshold, i.e. it is determined whether the heart is in a condition in risk of tachycardia (product in the range K below the hyperbola according to FIG. 1) or in a non-critical condition (range U above the hyperbola).

If a condition in risk of tachycardia is determined, an antitachycardia stimulation of the heart by way of the microelectrode array 2 is initiated by the control unit 1 via the two output channels 21, 22 which have an output amplifier 19, 20 each.

Based on FIGS. 4 and 5, the structure of the microelectrode array 2 is described in short. The microelectrode array 2 is embodied as a planar microelectrode gate 23 (a so-called interdigital array (IDA)) which comprises meshing, finger-type electrode arms 3. Each electrode arm 3 consists of a conductive strip of precious metal (platinum, iridium or the like), which are placed in specially prepared surfaces on silicon chips and covered by a biocompatible, fluid-resistant and electrically insulating layer 24. On the finger structures, the layer configuration, which is comb-type in a plan view, has openings 25 of a diameter of 0.5 to 10 $\mu$m which ensure electric contact with the cell tissue. These openings represent the actual microelectrodes. The entire gate has a range of magnitude of approximately 1×1 mm$^2$.

The finger-type structure permits the acceptance of place and time dependent potentials of high resolution as well as the emittance to the cell tissue of current pulses of high current density, which can take place individually or simultaneously for each finger system, owing to the control-unit-1-controlled connecting unit 4.

Advantages reside in the possibility of simultaneous stimulation and measurement taking place on varying electrode arms 3 of the microelectrode gate 23. Electrode technology further permits to form planar chip electrodes into spherical formations by electroplating or gray tint lithography and also to combine them spatially or planarly to form composite systems of various chips.

The application of interdigital arrays is fundamentally known for electroanalytical purposes for instance from the article of M. Paeschke et al., "Properties of interdigital electrode arrays with different geometries", Analytica Chimica Acta 305 (1995), pages 126 to 136. The microelectrode array according to the invention is an advancement of the basic concept there shown, in which however the entire comb structure is electrically conductive and consequently in the form of an electrode.

In particular during the measurement of the above-specified MAP, the microelectrodes illustrated are of special importance as regards their electric properties. The phase boundary between the electrode and the cardiac muscle tissue can be characterized electrically as a connection in parallel of a capacitor (the so-called "Helmholtz capacity") and a resistor (the so-called "Faraday resistance"). The electrodes exhibit a phase boundary impedance of this array sufficiently low for the measuring of action potentials when they have suitable surface coats. This can be achieved by fractal or electroactive coating. Another advantage resides in the fact that by reason of the gate array, the favorable electric properties of microelectrodes are maintained, such as a high current density during stimulation and a wide frequency range of the measuring signal during observation caused by the dominance of the spherical diffusion portion as opposed to the linear portion. The application of such microelectrode gates is for instance known from U.S. 4,969,468 A1 for measurements taken on cell tissues or organs. However, measuring is only capacitative in this case, because the virtual electrodes are covered by a dielectric layer.

Summing up, it may be said that in the case of the present application and according to the invention, the refractory time and the stimulus conduction velocity in the cardiac muscle tissue are sensed by a microelectrode gate, comparison of the product of the two values mentioned with respective threshold values being sufficient to be able to decide whether the heart is in a condition of risk of tachycardia. Based on threshold values, a tachycardia condition that may have set in can be classified, depending on the danger to the patient, and adequate therapy can be selected by the system. By the aid of the ultramicroelectrodes according to the invention, measuring signals of a substantially improved signal/noise relationship and a substantially expanded frequency range during observation can be obtained due to specially advantageous diffusion conditions. Moreover, a current density increased by orders of magnitude is possible during stimulation processes.

Finally, attention is drawn to the fact that FIG. 3 is only a functional and block-diagram-type illustration of the apparatus according to the invention. This apparatus is put into practice on a microprocessor basis, controlled by functional, operational programs, as is known from heart pacemaker technology. Correspondingly, the control unit 1 can be reprogrammable telemetrically from outside so that the apparatus according to the invention for early tachycardia diagnosis can be adapted to changing cardiologic framework conditions.

What is claimed is:

1. An implantable apparatus of the early diagnosis and suppression of tachycardia in the heart, comprising
    a microelectrode array (2), which is in contact with cardiac muscle tissue, for detecting stimulus conduction potentials in the cardiac muscle tissue,
    a measuring device (9, 10, 11), which is in connection with the microelectrode array (2), for determining a refractory time (tR) of cardiac muscle cells in a monitored cardiac muscle region,
    a measuring device (12, 13, 14, 15), which is in connection with the microelectrode array (2), for determining a stimulus conduction velocity (v) in the monitored cardiac muscle region,
    a computing device (17) for determining a product value of the refractory time (tR) and the stimulus conduction velocity (v),
    a comparator (18) for comparing the product value with a tachycardia threshold (T), any falling short of the tachycardia threshold (T) signaling a condition of the heart in risk of tachycardia,
    a stimulation arrangement (19, 20, 21, 22) for generating an antitachycardia stimulation upon detection of a condition of risk of tachycardia in particular via the microelectrode array (2), and a control unit (1) for controlling measuring and evaluation processes within the apparatus.

2. An apparatus according to claim 1, wherein the microelectrode array (2) is a planar microelectrode gate (23) with meshing, finger-type electrode arms (3).

3. An apparatus according to claim 1, wherein the microelectrode array (2) is positioned on an electrode probe to be inserted into a heart's ventriculus or atrium.

4. An apparatus according to claim 1, wherein for determination of the refractory time ($t_R$) and the stimulus conduction time (v), pairs of electrode arms (3) of the microelectrode array (2) are variably selectable by means of the control unit (1) via a connecting unit (4).

5. An apparatus according 4, wherein the selected electrode arms (3) can be coupled with two input channels (5, 6), in each of which threshold comparators (9, 12) are interconnected for signal detection.

6. An apparatus according to claim 5, wherein the threshold comparators (9, 12) are provided with time function elements (10, 14) for determination of the refractory time ($t_R$) and the stimulus conduction time (v) between the two selected electrode arms (3).

7. An apparatus according to claim 6, wherein a computing element (16) for calculating the stimulus conduction velocity (v) from the stimulus conduction time and a distance (a), preset by the control unit (1), of the selected electrode arms (3).

8. An apparatus according to claim 1, wherein the control unit (1) is followed by two output channels (21, 22) comprising output amplifiers (19, 20) as a stimulation device.

9. An apparatus according to claim 1, wherein the measuring, computing, comparator and control devices (1, 9, 10, 11, 12, 13, 14, 15, 16, 17, 18) are put into practice on a microprocessor basis, controlled by functional, operational programs.

10. An apparatus according to claim 1, wherein the apparatus is reprogrammable preferably telemetrically from outside.

11. An apparatus according to claim 1, wherein the microelectrode array (2) in the form of a microelectrode gate (23) which has electrode arms (3) meshing in the way of fingers comprises an insulating layer (24), the openings (25) of which located over the electrode arms (3) constitute the microelectrodes.

* * * * *